(12) United States Patent
Decker et al.

(10) Patent No.: US 9,990,560 B2
(45) Date of Patent: Jun. 5, 2018

(54) TEST STRIP MOBILE APP SYSTEM AND METHOD

(71) Applicant: Digital Concepts of Missouri, Inc., Maryland Heights, MO (US)

(72) Inventors: Paul Decker, Creve Coeur, MO (US); Jack Greenwood, St. Peters, MO (US)

(73) Assignee: Digital Concepts of Missouri, Inc., Maryland Heights, MO (US)

( * ) Notice: Subject to any disclaimer, the term of this patent is extended or adjusted under 35 U.S.C. 154(b) by 0 days. days.

(21) Appl. No.: 15/019,236

(22) Filed: Feb. 9, 2016

(65) Prior Publication Data

US 2016/0232421 A1   Aug. 11, 2016

Related U.S. Application Data

(60) Provisional application No. 62/113,799, filed on Feb. 9, 2015.

(51) Int. Cl.
| | | |
|---|---|---|
| *G06K 9/46* | (2006.01) | |
| *G06K 7/14* | (2006.01) | |
| *G01N 21/78* | (2006.01) | |
| *G06K 19/06* | (2006.01) | |
| *G06K 7/10* | (2006.01) | |
| *G01N 21/77* | (2006.01) | |

(52) U.S. Cl.
CPC .......... *G06K 9/4652* (2013.01); *G01N 21/78* (2013.01); *G01N 2021/7759* (2013.01); *G01N 2201/0222* (2013.01); *G06K 2007/10524* (2013.01); *G06K 2019/06253* (2013.01); *G06K 2209/03* (2013.01)

(58) Field of Classification Search
CPC .................................................. G06K 9/4652
USPC ........................................................... 422/552
See application file for complete search history.

(56) References Cited

U.S. PATENT DOCUMENTS

| | | | |
|---|---|---|---|
| 8,145,431 B2 | 3/2012 | Kloepfer et al. | |
| 8,655,009 B2 * | 2/2014 | Chen | G01N 21/274 382/100 |
| 8,734,734 B2 | 5/2014 | Kido et al. | |
| 8,797,180 B2 | 8/2014 | Weintraub et al. | |
| 8,824,800 B2 | 9/2014 | Bremnes et al. | |
| 2010/0254581 A1 | 10/2010 | Neeser et al. | |
| 2011/0111522 A1 * | 5/2011 | Zimmerie | A61B 10/007 436/501 |
| 2014/0017802 A1 * | 1/2014 | Smith | G01N 21/78 436/164 |

(Continued)

FOREIGN PATENT DOCUMENTS

WO    2011/141908 A2    11/2011

OTHER PUBLICATIONS

LaMotte "Mobile WaterLink Spin" http://www.lamotte.com/en/pool-spa/digital-testing/3577.html, Mar. 9, 2015, 2 pages.

(Continued)

*Primary Examiner* — Jill A Warden
*Assistant Examiner* — Jacqueline Brazin
(74) *Attorney, Agent, or Firm* — Senniger Powers LLP

(57) ABSTRACT

A mobile device reads a test strip to determine a chemical condition of a fluid. The mobile device transmits the determined chemical condition to a fluid treatment system which treats the fluid in response to the determined chemical condition.

18 Claims, 13 Drawing Sheets

(56) References Cited

U.S. PATENT DOCUMENTS

2014/0072189 A1* 3/2014 Jena ............... G01N 21/8483
382/128
2014/0107939 A1 4/2014 Jaunakais et al.
2014/0212336 A1 7/2014 Kido et al.
2015/0029037 A1 1/2015 Weintraub et al.

OTHER PUBLICATIONS

LaMotte "Insta-TEST Pool and Spa Test Strips" http://www.lamotte.com/en/pool-spa/insta-test?tab=Pool%20and%20Spa%20Test%20Strips, Mar. 9, 2015, 3 pages.
Insta-Link Home Subscription Features, http://www.insta-link.com/learn_morehome.html, Mar. 9, 2015, 3 pages.
Insta-Link Home FAQ, http://www.insta-link.com/support.php, Mar. 9, 2015, 2 pages.
Insta-Link Home Pool and Spa Water Testing Subscription and Mobile App Features, http://www.insta-link.com/learn_morehome.html, Mar. 9, 2015, 4 pages.
SL1000 Portable Parallel Analyzer (PPA), Hach USA, http://www.hach.com/sl1000-portable-parallel-analyzer-ppa/product-details?id=22361943508, Mar. 9, 2015, 2 pages.
McCoy, Kevin, NYC start-up's aim: Showing its true colors, USA Today, Jan. 5, 2015, 1 page.
AquaChek Pool & Spa Test Strips Water Testing Product Guide, AquaChek.com, 2013, 8 pages.
iTunes Clorox Test Strip App, https://itunes.apple.com/us/app/clorox-pool/id957130735?mt=8, printed May 31, 2017 (3 pages); see also Clorox Test Strip App video at https://www.youtube.com/watch?v=WvTCYOUHwEA, Aug. 3, 2015.
www.Cloroxpool.com screen shots printed May 31, 2017, 3 pages.

* cited by examiner

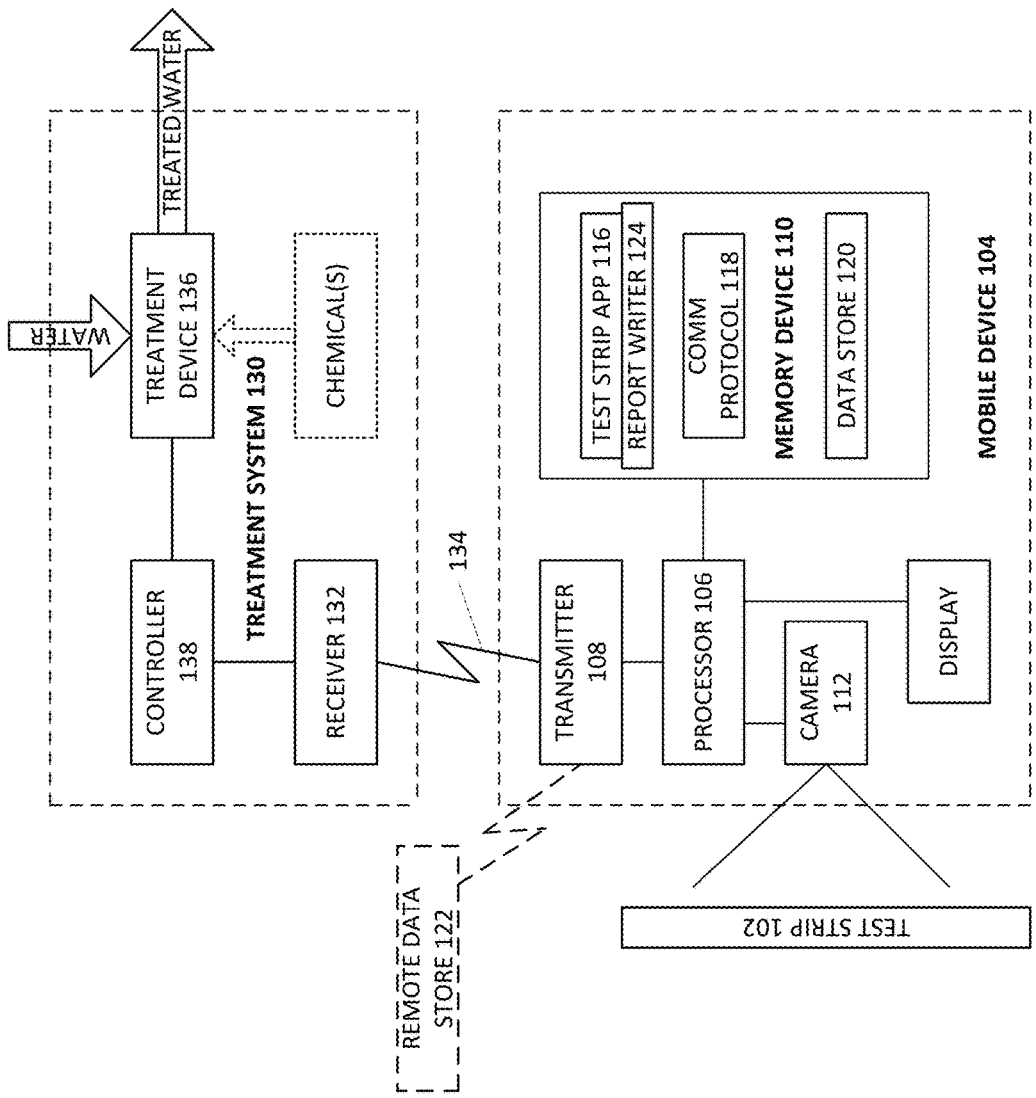

US 9,990,560 B2

TEST STRIP MOBILE APP SYSTEM AND METHOD

BACKGROUND

There is a need for a line of pool/spa products with advanced analytical and control features that will enhance the effectiveness of pool/spa products and implement the pool/spa products in a variety of applications.

SUMMARY

In one form, a platform is implemented in conjunction with a mobile phone or tablet APP to analyze and act upon pool and spa test strips. In particular, a mobile phone or tablet APP analyzes the color of test strips.

Provided herein are implementation details and some preliminary test data to support the approach. In addition, design details such as software frameworks and libraries used are provided.

BRIEF DESCRIPTION OF THE DRAWINGS

FIG. 13 is a block diagram of one embodiment of a system according to the invention.

Corresponding reference characters indicate corresponding parts throughout the drawings.

DETAILED DESCRIPTION

Advances in the cameras and processing power of smart phones and tablets make them a platform for running computer vision algorithms and processes to provide accurate test strip analysis which does not depend on a user comparing colors on a test strip to a reference. Algorithms in computer vision are used to detect objects and their colors (in this case a pool/spa test strip). Initial testing has indicated that a test strip can be detected and analyzed by using square detection and finding squares in close proximity to each other and in line, while minimizing false positives.

To enhance the effectiveness in one embodiment, a machine-readable code can be placed on the test strip. For example, a code readable by a mobile device can be use such as a bar code or a QR code if the strip is wide enough to accommodate the minimum QR code size to get sufficient resolution for readability. Placing a code on the test strip allows the APP to simply search for a code initially, rotate the image based on the code, and then apply advanced object detection routines to determine a location and color of the test strip pads.

Furthermore, adding a code to the strip provides additional benefits including but not limited to:

The code can be used to encode the strip manufacturer. This can be used for the following:
1. The code can be set up to only work with certain manufacturers.
2. The APP can use the manufacturer information encoded on the code to look up (e.g., utilize a look-up table in a cloud database) the test square layout, including a number and size of the squares, and what the different colors mean to determine test results.

The code can encode the expiration date. This can be used for the following:
1. If the code is expired, the user can be warned.
2. If the code is about to expire, the user can be asked if they would like to purchase more strips and could do so directly from the application.

The code can be printed in a well-known color (i.e. red) and this can be used for camera calibration The code can also encode other tracking information.

Figure 1:
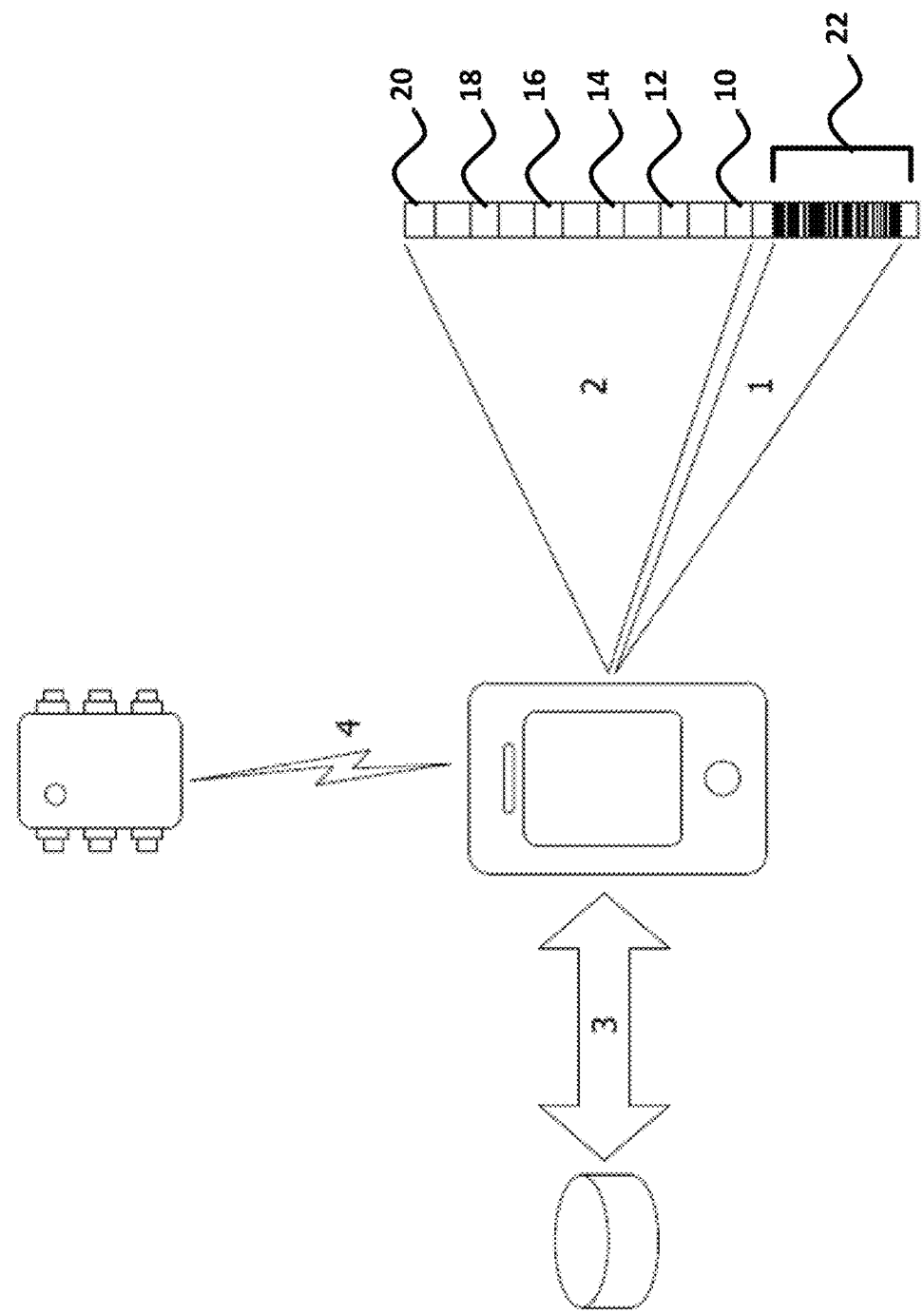
FIG. 1 is an illustration of a system overview according to one embodiment of the invention.

Based on the embodiment in which the test strip has a QR code, one implementation provides the capability of analyzing test squares on the test strip and transmitting instructions to a user, as illustrated in FIG. 1. During implementation of aspects of the system, generally indicated at 1, the APP detects via the camera a QR code 22 to confirm that a test strip has been placed in front of the camera (in this example, a tablet or smart phone camera). In an exemplary embodiment, the APP includes processor-executable instructions, stored in a computer-readable storage medium and executed by a processor of a computing device (e.g., a tablet or a smart phone), for acquiring visual image data of the test strip via the camera. During further implementation of aspects of the system, generally indicated at 1, the APP reads the QR code 22 on the strip to determine the manufacturer and other pertinent information (described in more detail herein). In an exemplary embodiment, the APP includes processor-executable instructions that adapt the computing device for identifying bar codes in image frames captured by the camera.

The APP detects the test squares (e.g., squares 10-20 as described in more detail herein) on the strip with regard to their position relative to the detected QR code and determines their color during implementation of aspects of the system generally indicated at 2. In an exemplary embodiment, the APP includes processor-executable instructions that adapt the computing device for identifying the test squares based on the barcode location and determining a color of each test square in image frames captured by the camera.

During additional implementation of aspects of the system, generally indicated at 3, the APP looks up the meaning of the color of each test square in internal storage devices and/or external storage devices (i.e. a file or database). In an exemplary embodiment, the APP includes processor-executable instructions that adapt the computing device to transmit data regarding the color of each test square to a database via a communications network (e.g., the Internet) and receive data indicative of an indication of a pH range associated with each color. During implementation of aspects of the system, generally indicated at 4, the APP transmits the results back to a user (in one example, a pool/spa control board). In an exemplary embodiment, the APP transmits water treatment instructions, via a communications network (e.g., Bluetooth, Wi-Fi, etc.), to a control device associated with a pool or spa for treating the water of the pool or spa in accordance with the transmitted instructions. By operating in this manner, aspects of the system act (e.g., control a treatment device) upon analysis of the test strips.

Figure 2:
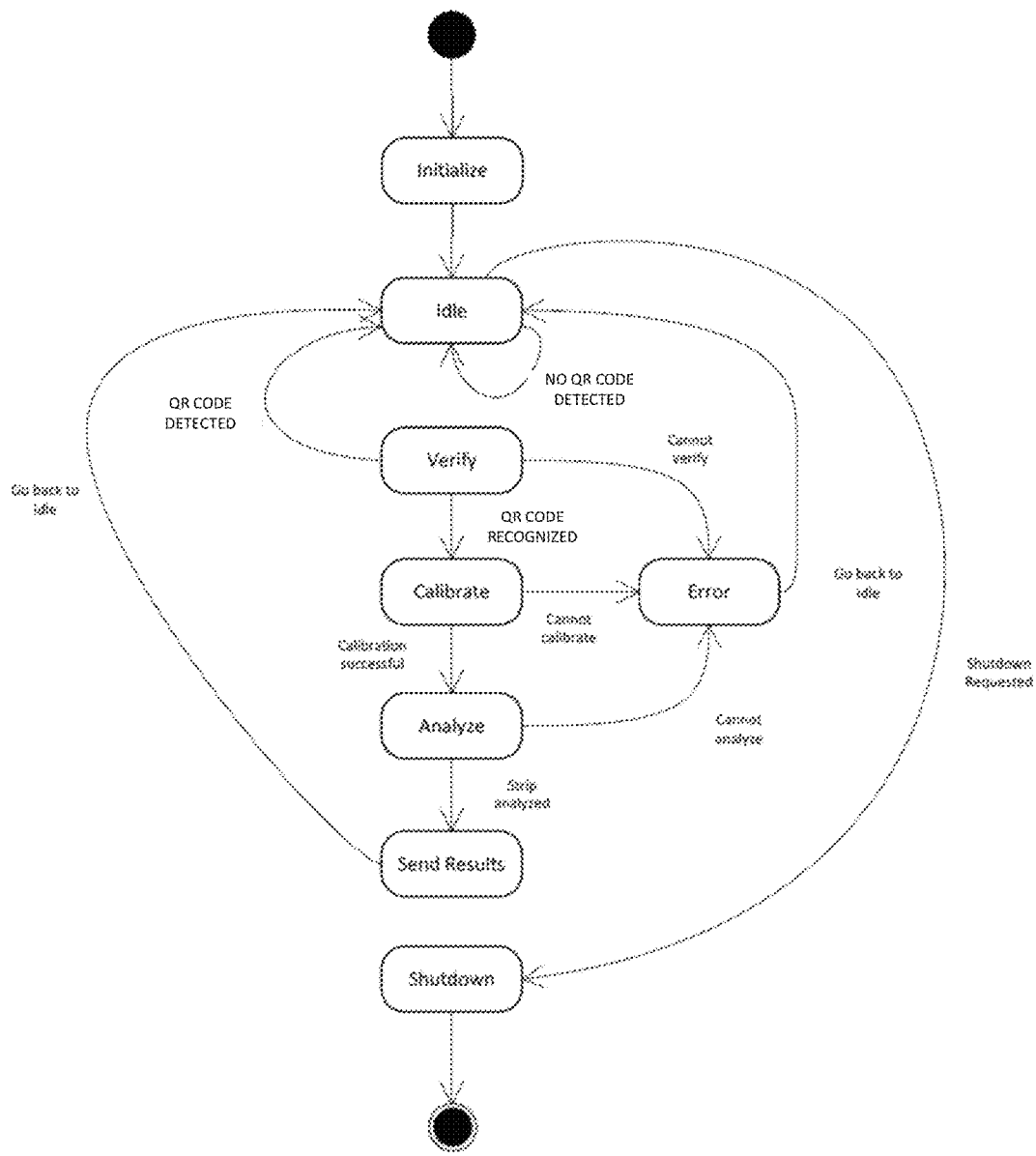
FIG. 2 is a block diagram of a high level state machine according to one embodiment of the invention.

At a high level, the APP system flow can be broken into eight unique states. The states are generally summarized as follows and are illustrated in block diagram form in FIG. 2. In one form the APP is for use with a test strip configured to indicate a chemical condition of a fluid in which the test strip has been immersed. The APP is configured to be executed by a mobile device having a processor, a memory device, and a camera configured to read the test strip. The APP comprises processor executable instructions configured to be stored in the memory device and configured to be executed by the processor. In one form, the instructions comprise instructions to:

Initialize—This is the first state the APP system enters upon start-up. In this state all software libraries will be initialized (such as the machine vision library and the QR code reader library). The APP system will also initialize any other data and attempt to connect to external data sources (such as a database) if required.

Idle—In this state the APP system continuously scans for a QR code. If a QR code is found, it will transition to the next state; otherwise, it will keep scanning.

Verify—In this state the QR code which has been found is checked to make sure it is a recognized one. If the QR code is recognized the APP system will continue. If it is not recognized the APP system will transition back to idle.

Calibrate—In general, the camera can be optionally calibrated. In one form, the QR code is printed in a known color to aid in calibration. Based on this color the camera can be calibrated for this particular read of the test strip.

Analyze—Based on the QR code location and manufacturer information, the test squares will be located and their color will be analyzed. The meaning of the colors will either be stored in the APP itself or in an external data source (such as a cloud database). In one form, the instructions to analyze comprise:

instructions configured to locate one or more pads on the test strip;
instructions configured to determine a color of each located pad;
instructions configured to compare the determined color to a reference; and
instructions configured to determine the chemical condition indicated by each pad based on the comparison.

Send Results—Once the strip has been analyzed, the results will be sent to the interested user (e.g., an operator or a pool/spa controller) for further action.

Error—This state is entered any time another state cannot properly complete. Clean up will occur in this state and then the APP system will transition back to Idle.

Shutdown—This state is entered any time after the idle state in response to a manual command, a time-out, or a specific, pre-defined condition.

Figure 3:
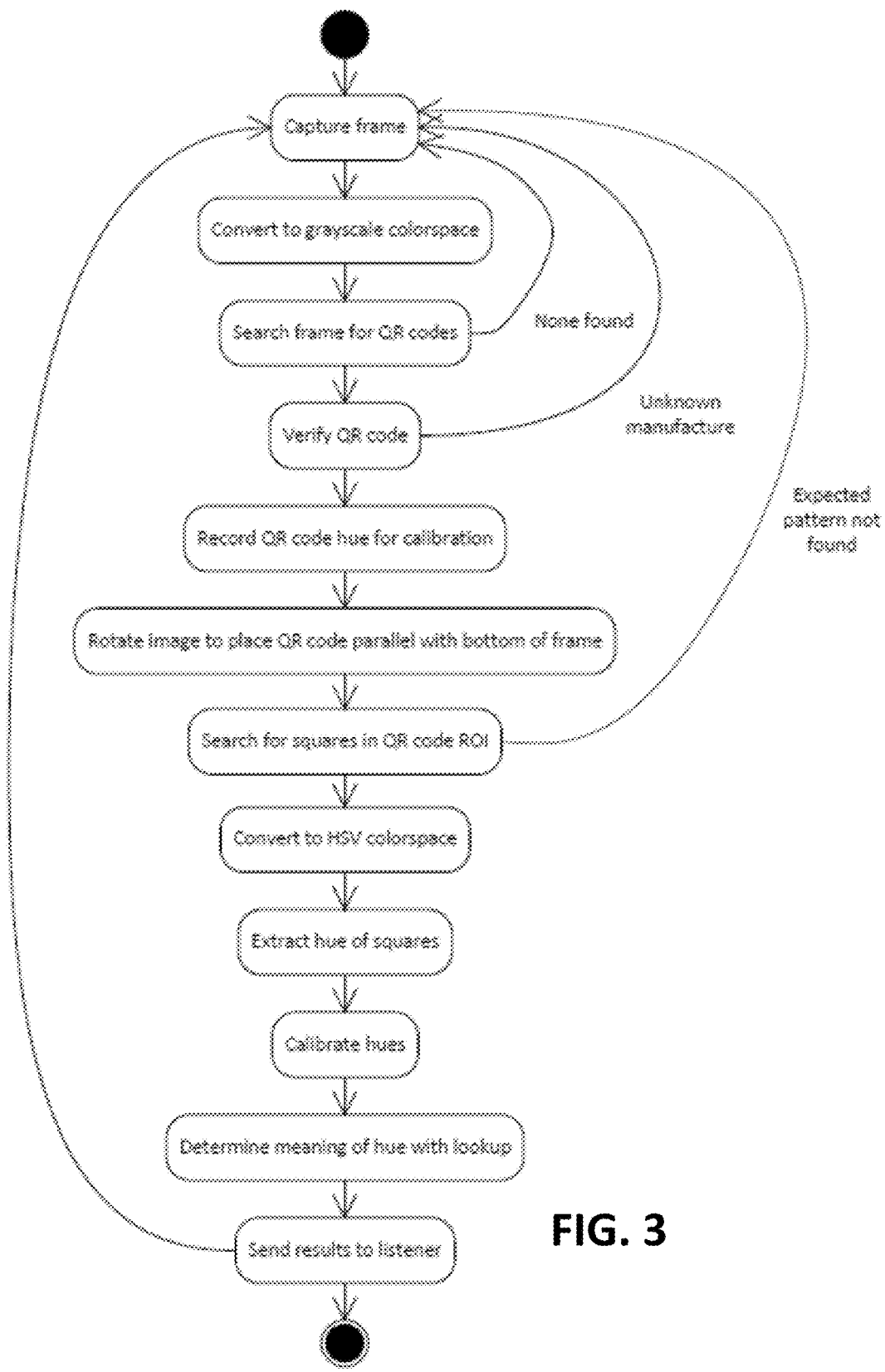
FIG. 3 is a block diagram of a frame analysis pipeline according to one embodiment of the invention.

A detailed state machine describing the analysis instructions that are executed by the processor of the mobile device when each frame is captured and analyzed is illustrated in block diagram form in FIG. 3. In one form, the frame processing state machine works as follows based on processor executable instructions for the following.

1) A frame is captured from the onboard camera and fed into the image processing pipeline.
2) The frame is converted to grayscale.
3) The frame is fed into the code detection algorithm to search for QR codes. If no QR code is found, the pipeline is exited and a new frame is captured.
4) If a QR code is found, the QR code is verified against predefined criteria such as:
    Correct form or format
    Acceptable manufacturer
    The calibration strip is not expired
    Other pre-defined criteria
5) The hue of the QR code is recorded for calibration purposes. Based on the known hue of the QR code and the recorded hue from the camera, the camera can be calibrated.
6) The image is rotated based on the QR code position, the beginning of the QR code, and its size to place the QR code parallel with the bottom of the frame with the start position of the code on the left.
7) The region of the image next to the QR code is run through a Haar classifier to guarantee that test strip pattern of test squares if found. Currently, this is just an added, optional check to confirm that the machine vision is working correctly; this check can be removed. If the Haar classifier does not find the features it is searching for (in this case multiple test squares in a row) the pipeline is exited and a new frame is captured.
8) Search the ROI (region of interest) found by the Haar classifier for the individual test squares and note the locations. Further details regarding square detection are provided herein.
9) Convert the ROI to HSV (Hue, Saturation Value) colorspace. HSV colorspace is preferable to RGB (red, green, blue) for color detection as it will minimize the effects of the lighting (sunlight, poor lighting, flash).
10) Extract the hue of each test square.
11) Determine the meaning of the square hue via an internal lookup or and external data source (database or file).
12) Send the results to the user (e.g., via Bluetooth or Wifi).

Optional App Implementations

In one embodiment, the test strip APP 116 can be configured to store test strip data readings (e.g., pad/square color) or other data input by a user in a data store 120, such as in memory device 110, or to store the data at a remote location such as a remote data store 122 on a site by site basis (cloud or otherwise). In addition, the APP 116 could include a report writer 124 to selectively access the stored data to generate a report from stored data. The data and/or reports could be provided to users, such as a pool service company, pool owners, and other customers. For example, the data and reports could be maintained at hotels to show conformance with health department regulations or other requirements.

It is also contemplated that the APP 116 be configured with instructions so that it could also be used as a chemical calculator driven by the readings of the test strip 102. For example, a data field could be added to the APP 116 allowing a user to input the size of a body of water to be treated and a zip code of the location. Based on the readings from the test strip 102, a lookup table could be used to provide treatment information regarding the amount of chemicals needed to get the water within health department ranges based on the zip code of the pool.

Also, another alternative option is encoding a date of manufacture or an expiration date of a test strip 102 within the QR code on the strip. The APP 116 could read the QR code and recognize the date on the test strip and, in response, could notify a user regarding the date and suggesting buying more strips as the expiration date of the strip get close. Further, the APP 116 can be configured to communicate with a seller so that a user could have a one touch buying experience (e.g., the APP 116 could be linked to an Amazon® account).

In yet another alternative embodiment, the APP 116 is configured to provide chemical dosages. In accordance with this embodiment, the APP 116 is configured to store properties associated with a pool/spa in a data store 120, such as in memory device 110 and/or remote data store 122. For example, the APP 116 may receive user input regarding properties associated with a pool such as length, width, water depth, volume, inventory of treatment chemicals, and the like. The APP 116 may develop and store an inventory of chemicals by utilizing captured images of barcodes (e.g., UPC barcode) associated with the chemicals. Developing an inventory of chemicals by capturing images of the barcodes associated with those chemicals allows the APP 116 to determine properties of the chemicals that may not be available through manual user input. For example, scanning a UPC barcode associated with a certain commercial embodiment of a chemical allows the APP 116 to determine a strength (e.g., percent calcium chloride) of the chemical. Utilizing a known volume of the pool (e.g., 500 gallons) and a property of the water in the pool (e.g., pH of 6.8), the APP 116 can access the stored chemical inventory to determine an amount of inventoried chemical to add to the water of the pool (e.g., one scoop of chlorine). In an embodiment, the chemical inventory is a look-up table stored in data store 120, such as in memory device 110 and/or remote data store 122 (e.g., a cloud database). In yet another embodiment, the APP 116 is configured to communicate with a seller to purchase a needed chemical that is not in the inventory, as further described herein.

Aspects of the APP 116 may provide an exemplary benefit to pool/spa service companies because untrained staff and/or customers can utilize the APP 116 to provide details of the pool/spa before a trained technician is dispatched.

Implementation Details

This section documents one embodiment of implementing the processes provided in the previous sections.

One embodiment is based on the following high level requirements:
1) The APP shall be configured as a cross-platform and run on the following platforms at a minimum:
   iOS
   Android
2) The APP detects the test strip without user intervention.
3) The APP shall be configured to work in multiple lighting conditions and inform the user if the current lighting conditions are unacceptable.
4) The APP shall be configured to transmit findings back to a pool/spa controller wirelessly (e.g., via Bluetooth or Wifi).

In order to satisfy the above requirements, the following software components can be employed in one embodiment.

QT Framework—The Application can be written in the QT framework so that it can be cross-compiled for all major OS distributions (including Windows, Linux, and OS X) as well as all major smart phone distributions (Android, iOS, Blackberry, and Windows Phone). More information is available at http://qt-project.org/.

OpenCV—The OpenCV computer vision framework will be used for all vision algorithms except for code detection. The OpenCV framework is cross-platform and is precompiled to run on Android, iOS, Windows, OS X, and Linux. (For example, see http://opencv.org/).

ZBar—ZBar is a cross-platform code reader. It can be used to find codes in frames captured by the device's camera and is precompiled for many platforms. (For example, see http://zbar.sourceforge.net/).

In order to confirm implementation, sample code was written to test the detection strategies. Illustrated photos of the test strip from the test Application (running in Windows and built on the QT Framework) are presented in FIGS. 4-9.

Figure 4:
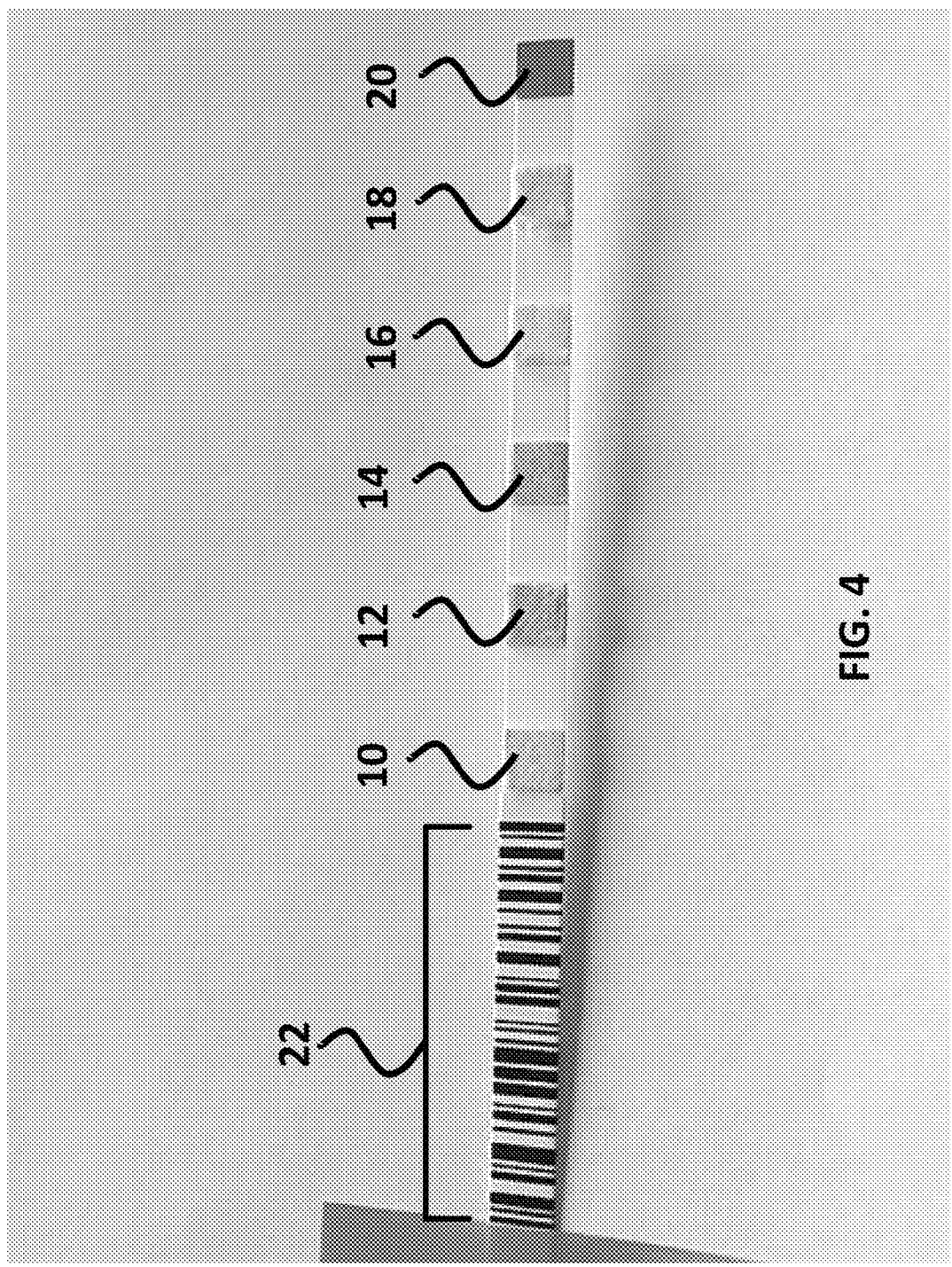
FIG. 4 is a photo of a test strip setup.

FIG. 4 illustrates the test strip setup. Illustrated is an off the shelf AquaChek 6-Way test strip to which a bar code has been added with "123456789" encoded in the bar code for testing. The test strip is taped to a white background to make the strip and its components easier to determine and distinguish, but the tests would work the same against most other backgrounds. In most cases, detecting objects against a white background is one of the hardest test cases.

The test strip in the embodiment illustrated by FIG. 4 includes squares 10, 12, 14, 16, 18, and 20 including chemical reagents associated with pH and a code 22 (e.g., bar code, QR code, etc.). In the illustrated embodiment, square 10 exhibits a substantially lemon-yellow color, square 12 exhibits a substantially pale-yellow color, square 14 exhibits a substantially orange-yellow color, square 16 exhibits a substantially white-yellow color, square 18 exhibits a substantially yellow color, and square 20 exhibits a substantially purple color. One having ordinary skill in the art will understand that the squares may exhibit other universal indicator colors and combinations and/or mixtures thereof, including red, orange/yellow, green, blue, and violet/purple.

Figure 5:
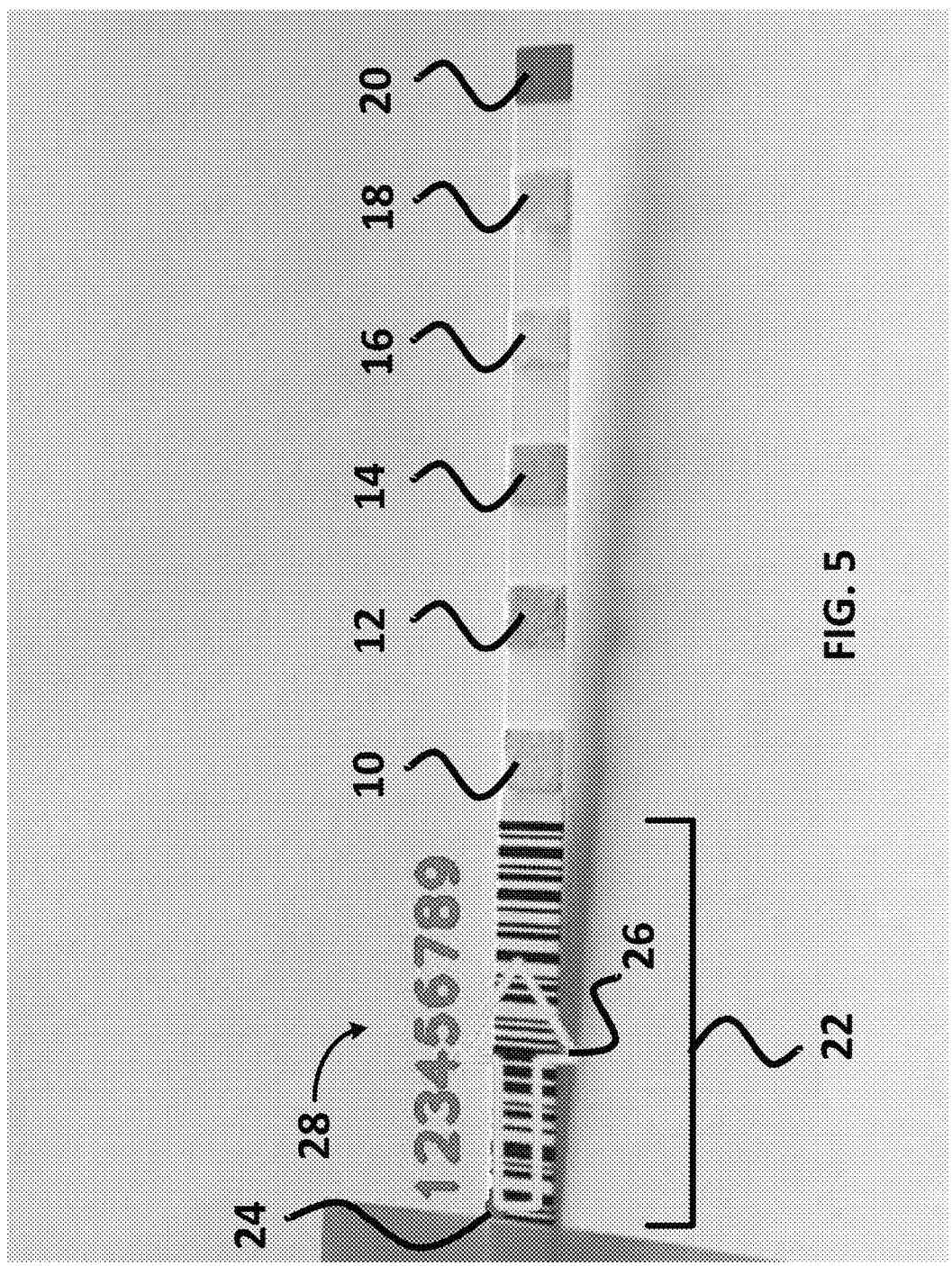
FIG. 5 is a photo of a test strip setup indicating bar code detection.

FIG. 5 illustrates that the software has detected the bar code 22. The start of the bar code is illustrated with a red dot 24 and an arrow 26 was superimposed by OpenCV to show the order in which the bar code was read. The red text 28 illustrates what the ZBar library read from the bar code which is correct.

Figure 6:
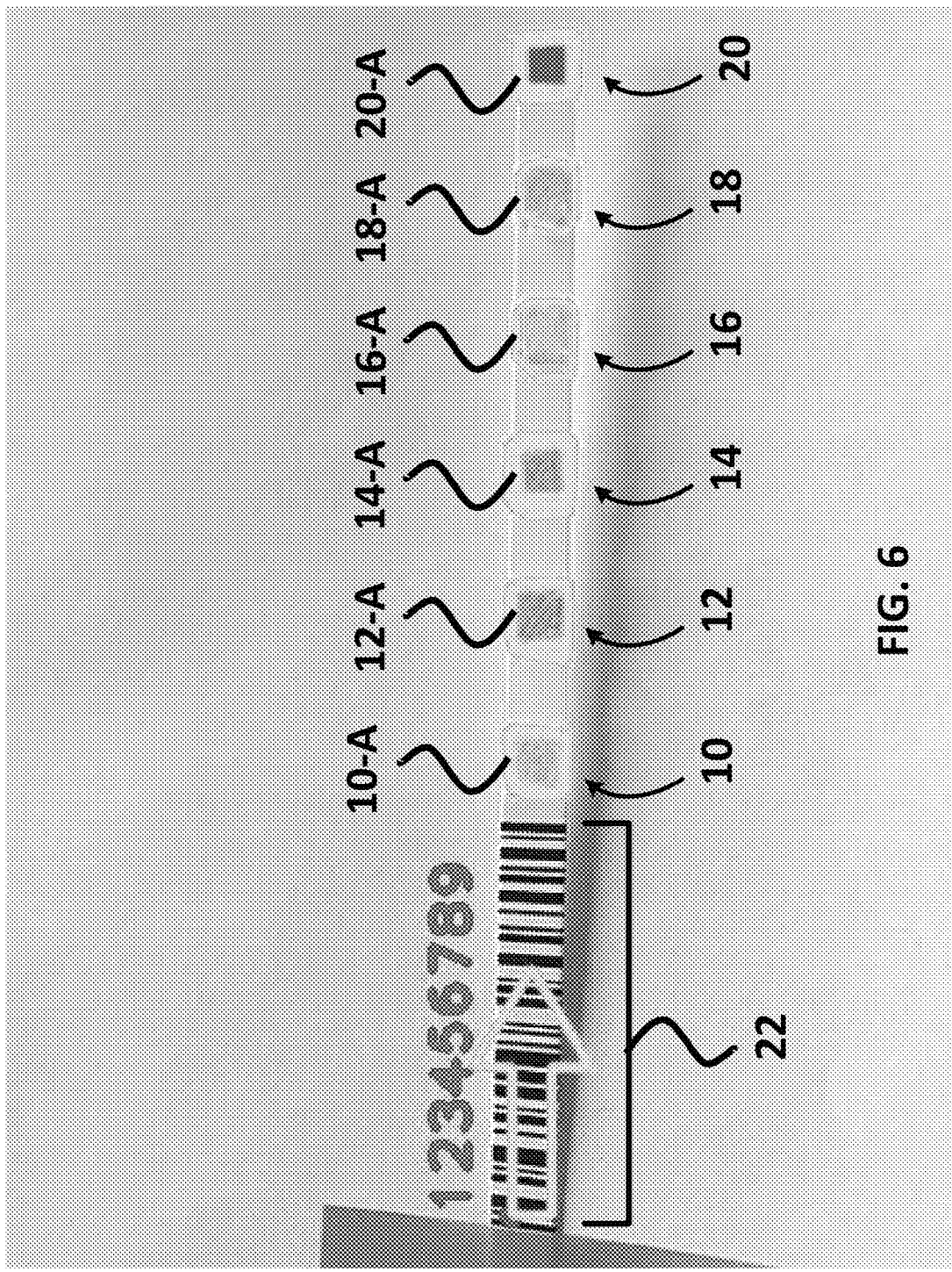
FIG. 6 is a photo of a test strip setup indicating square detection.

As illustrated in FIG. 6, after the bar code is detected, the squares are each detected in a confined region of interest based on and relative to the bar code location. Each region of interest is demarcated via a green line 10-A, 12-A, 14-A, 16-A, 18-A, 20-A around the perimeter of each region in the embodiment illustrated by FIG. 6.

Figure 7:
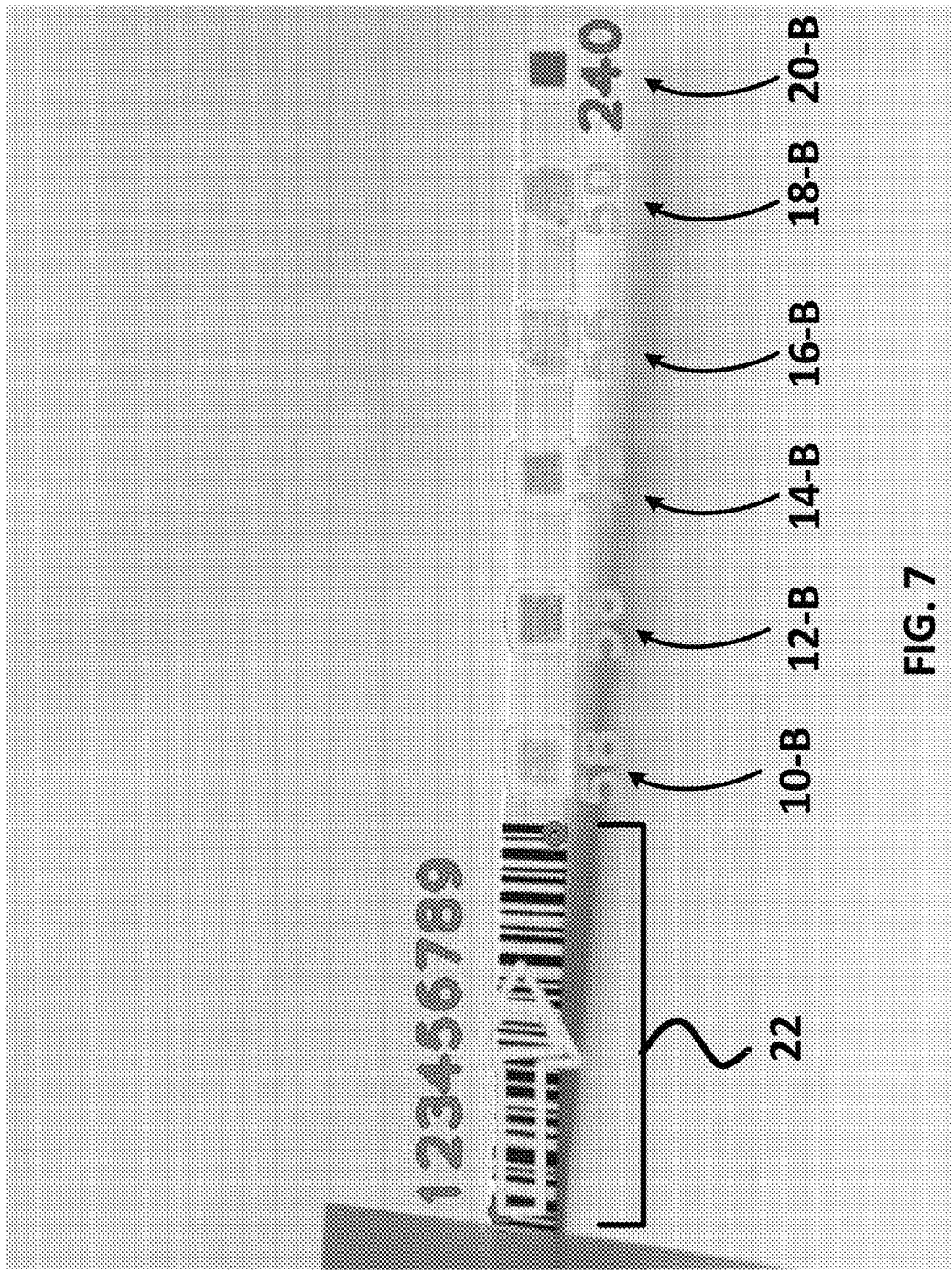
FIG. 7 is a photo of a test strip setup indicating hues detection.

Once the squares are detected the hues of each square are determined by averaging the hues of points in each square, as illustrated in FIG. 7. The text indicators 10-B, 12-B, 14-B, 16-B, 18-B, 20-B in FIG. 7 are each a numerical representation of the hues of each square 10, 12, 14, 16, 18, 20, respectively.

Figure 8:
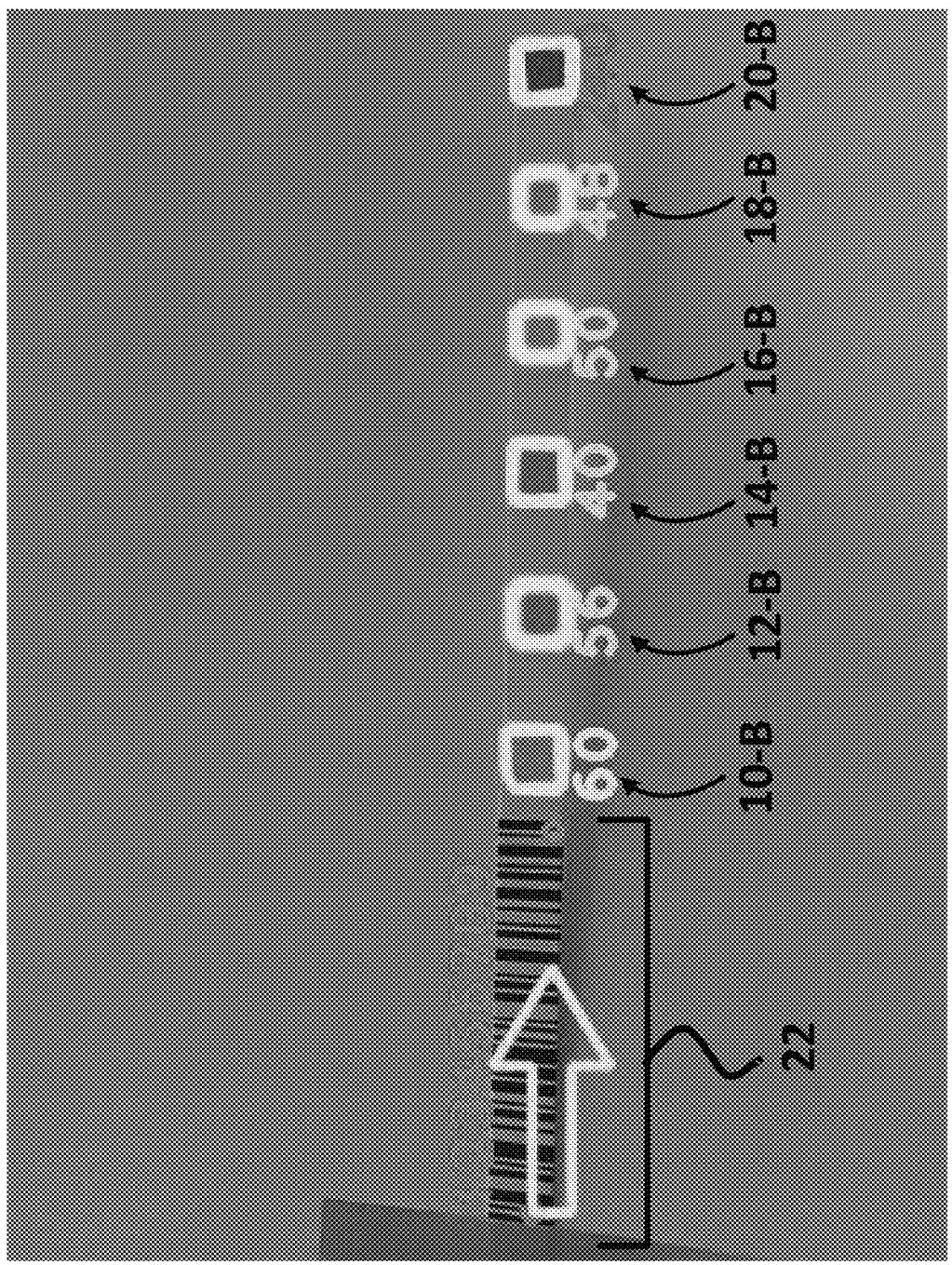
FIG. 8 is a photo of a test strip setup indicating low light condition detection.

To confirm low light operation, the same detection was run under low lighting conditions and the hue values stayed roughly the same as illustrated in FIG. 8.

Figure 9:
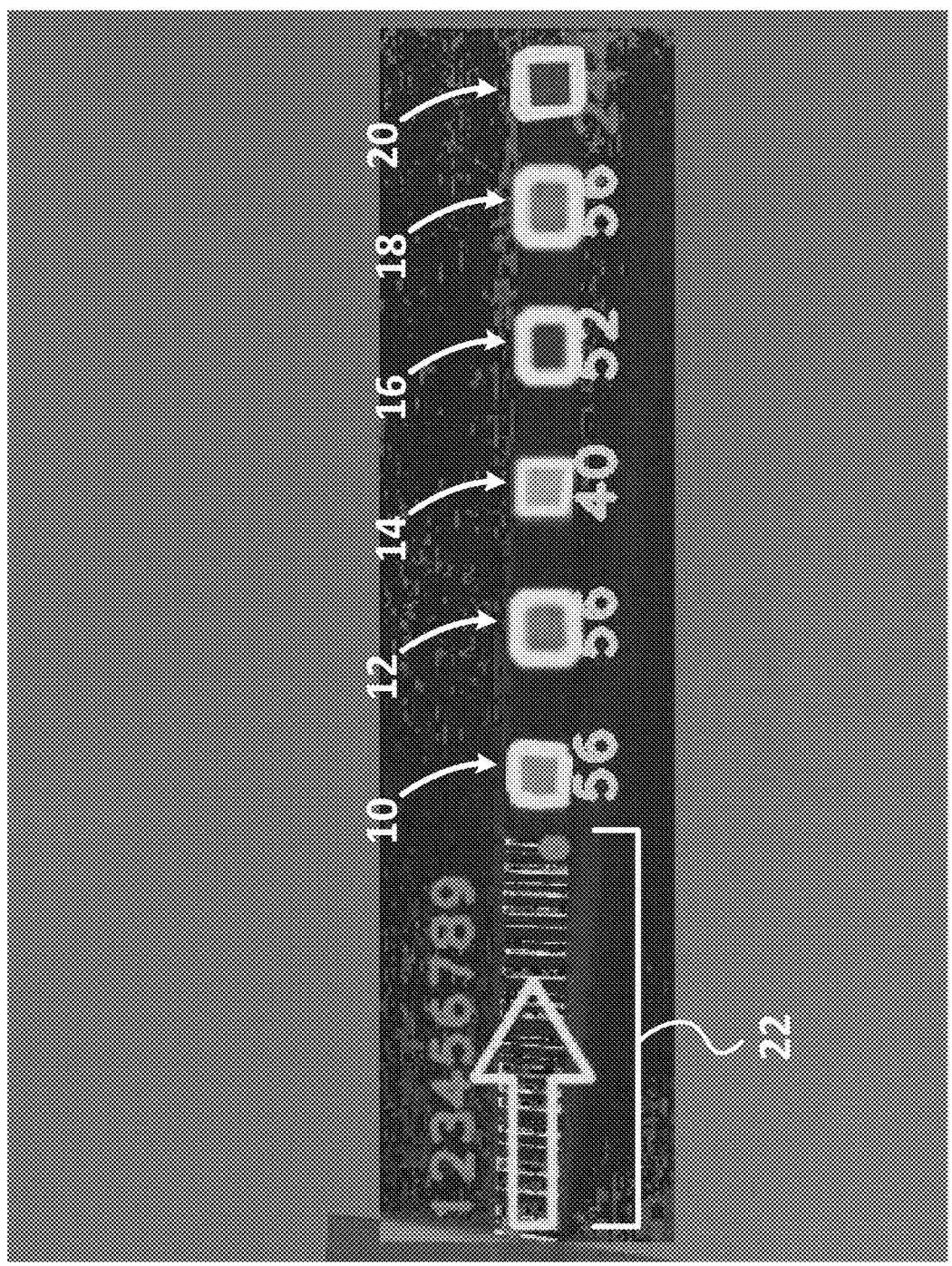
FIG. 9 is a photo of a test strip setup indicating HSV color space detection.

FIG. 9 illustrates the HSV color space which is what the machine vision library is actually using to detect the hues.

Initial investigation confirms the outlined process and implementation. All current data was collected on a Windows computer, but versions of the Application have also been run and effectively work on an iOS device.

The test strips of the invention can measure any one or more of the following: total hardness, high range hardness, low range hardness, total chlorine, bromine, free chlorine, pH, total alkalinity, cyanuric acid, temperature, color, total dissolved solids (TDS), salt, conductivity, copper, nitrites, phosphates, high-range chlorine, borates, iron, sodium bromide, and/or white salt titrators, and/or any other chemical or ion which can be measured by color testing.

Figure 10:
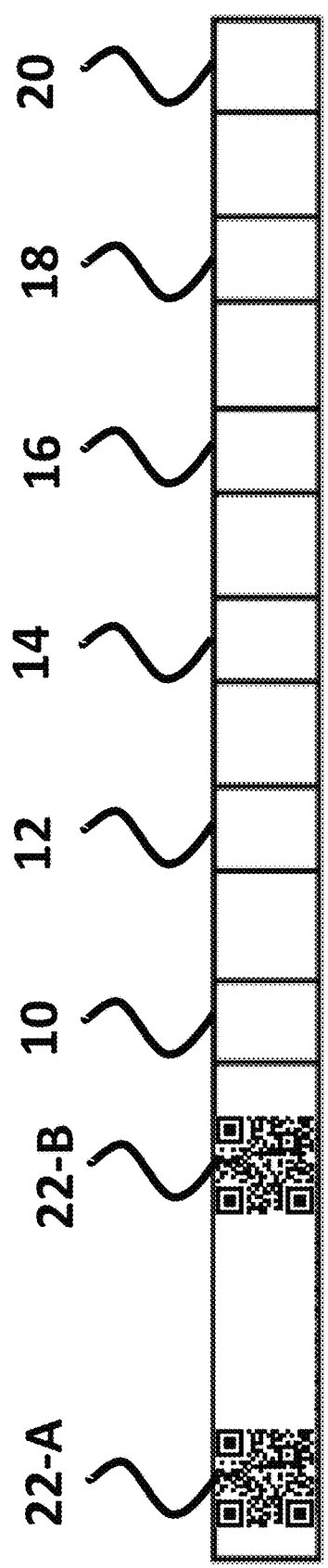
FIGS. 10 and 11 are diagrams of a test strip setup with multiple QR codes according to one embodiment of the invention.

FIG. 10 illustrates an embodiment of the test strip having multiple QR codes. In addition to the squares 10-20, this embodiment of the test strip includes a first QR code 22-A and a second QR code 22-B located on a handle of the test strip. In accordance with an aspect of the invention, QR code 22-A and/or QR code 22-B encode all of the strip metadata (e.g., strip manufacturer, expiration date, tracking information, etc.) at a lower resolution than an embodiment utilizing a single QR code. Beneficially, utilizing multiple QR codes allows each QR code 22-A, 22-B to be printed at a small size (e.g., to fit on a handle of the test strip) without a loss of quality. In another embodiment, the multiple QR codes 22-A, 22-B allow the APP to more accurately determine orientation of the test strip in a captured image and the location of the squares relative to the codes 22-A, 22-B, as further described herein. In accordance with a further aspect of the invention, an accurate determination of the strip orientation utilizing multiple QR codes 22-A, 22-B allows the APP to utilize fewer computing resources by foregoing computationally expensive computer vision routines.

Figure 11:
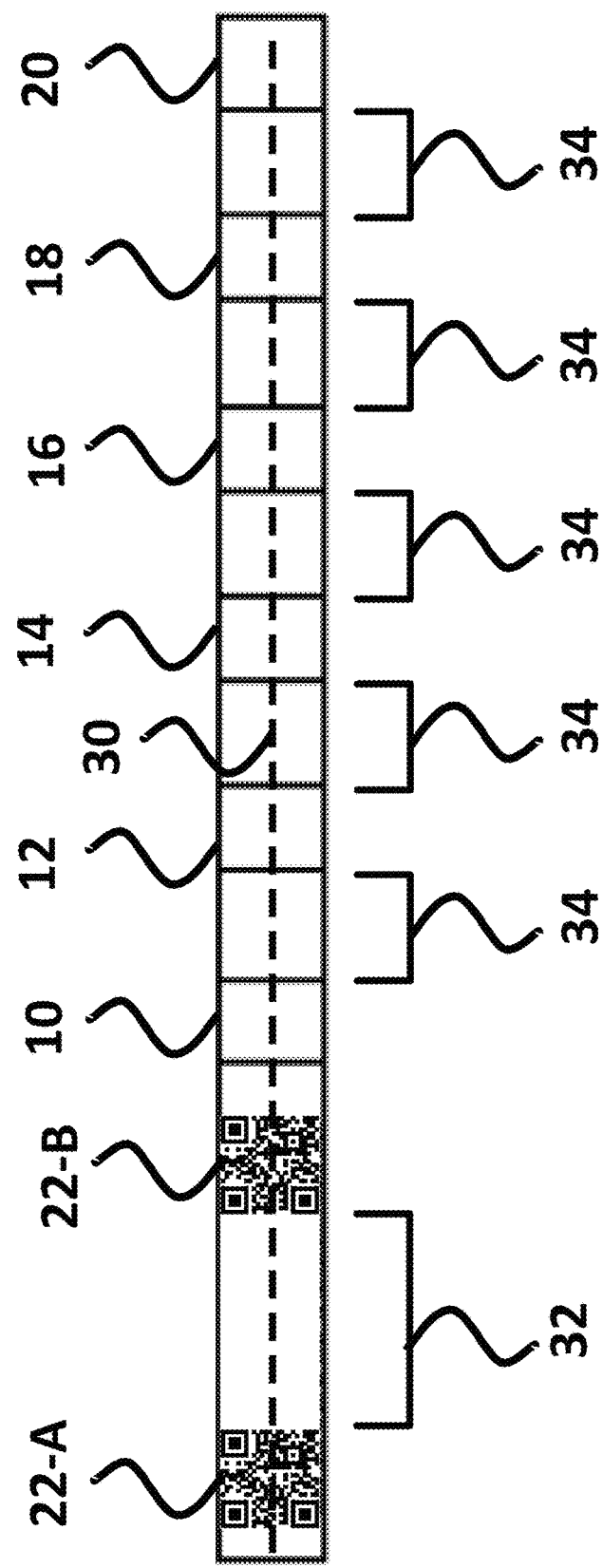

FIG. 11 illustrates aspects of a multiple QR code test strip utilized by a positioning algorithm implemented by the APP 116. In an embodiment, the QR codes 22-A and 22-B serve as two points on a line 30 along which squares 10-20 are located. In accordance with an aspect of the invention, utilizing the multiple QR codes 22-A, 22-B allows the APP 116 to more accurately determine the orientation of the test strip. For example, if a single QR code is utilized and the code is skewed relative to the test strip, the ability of the APP to detect squares 10-20 is hindered. In an embodiment, the APP 116 locates a substantially center point of each QR code 22-A, 22-B to define line 30. In another embodiment, the APP 116 utilizes a code interval 32 between the QR codes 22-A, 22-B to determine square intervals 34 between squares 10-20. In an embodiment, the code interval 32 is a substantially same distance as square intervals 34. In another embodiment, the code interval 32 is about half the distance as square intervals 34 (e.g., half-spacing). In accordance with an aspect of the invention, the APP 116 searches for squares 10-20 along line 30 beginning at QR code 22-B at distances substantially equal to the square interval 34 as a function of the code interval 32.

Figure 12:
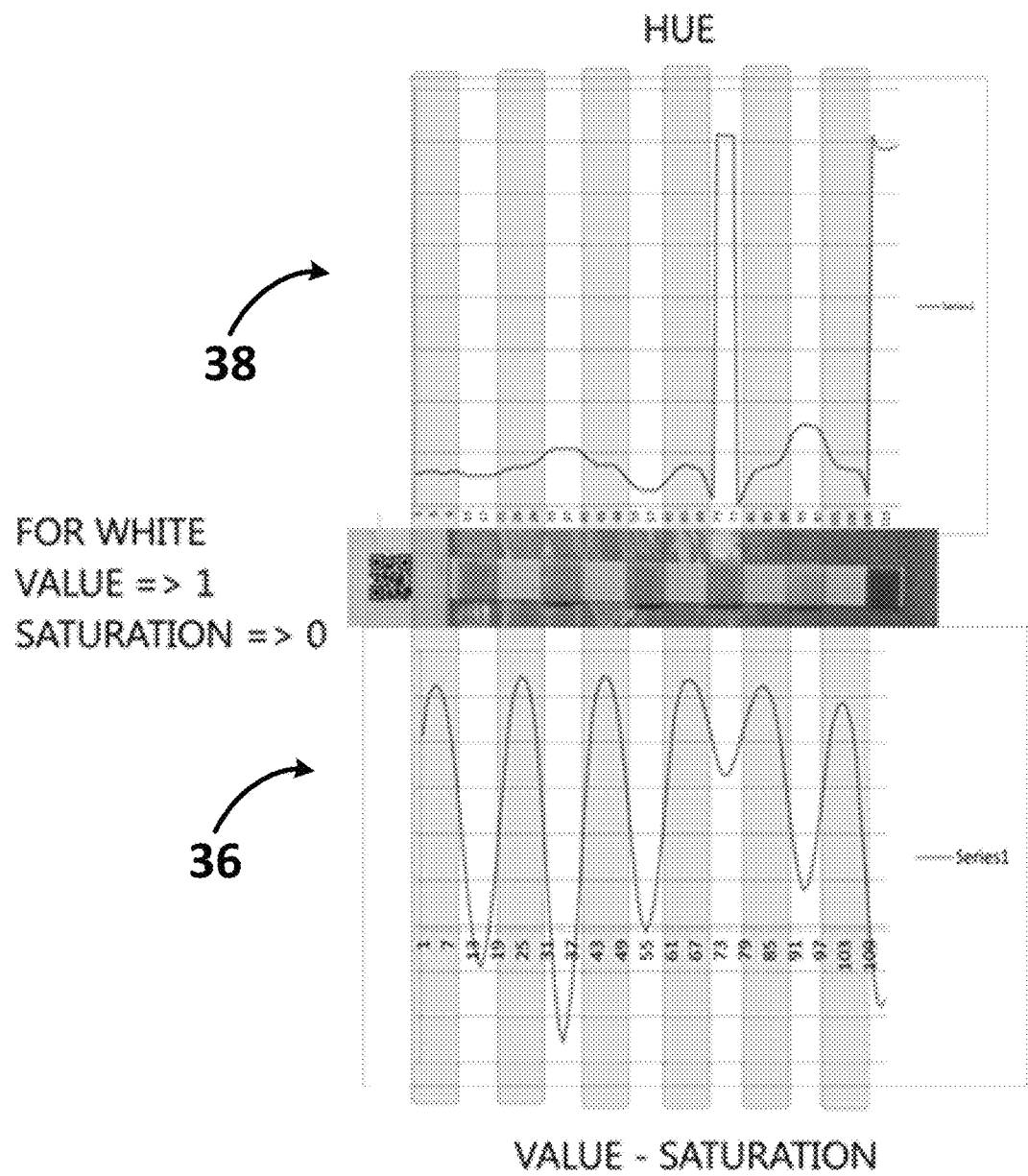
FIG. 12 is a graphical plot of a peak detection algorithm according to one embodiment of the invention.

In an embodiment, the APP 116 utilizes a detection algorithm over the length of the test strip to determine the position of squares 10-20. In one form, a white value peak detection algorithm determines the location of the white spaces between the squares 10-20 such that the hue value for each square can be sampled at positions between the white spaces. Alternatively, a trough detection algorithm can be used to determine the minimal white space which is indicative of the location of the squares 10-20. For example, the APP 116 samples and collects the result of subtracting the Saturation from the Value of the HSV colorspace at regular intervals across the strip. FIG. 12 illustrates a plot of the result of such subtraction at profile 36 and the corresponding Hues at profile 38 which are sampled at the troughs of profile 36. The illustrated embodiment is for a white Value of greater than or equal to one and a Saturation value greater than or equal to zero. The plot of the result of the subtraction at profile 36 is analyzed by the APP 116 to find the peaks, which represent the center of the interval between squares 10-20, and the troughs, which represent the center of each square 10-20.

FIG. 13 is a block diagram of one embodiment of a system according to the invention. FIG. 13 illustrates a system 100 for treating a fluid (e.g., pool/spa water) and for use with a test strip 102 configured to indicate a chemical condition (e.g., chlorine level) of the fluid. In an embodiment, test strip 102 comprises squares 10-20 and/or code 22 (e.g., barcode, QR code, etc.). A mobile device 104 having a processor 106, a transmitter 108, a memory device 110, a camera 112, and a display 114 is configured to read the test strip 102. A test strip APP 116 comprising processor executable instructions configured to be stored in the memory device 110 is configured to be executed by the processor 106. As noted herein, the App 116 includes the following instructions:

instructions configured to locate one or more pads on the test strip 102;
instructions configured to determine a color of each located pad;
instructions configured to compare the determined color to a reference;
instructions configured to determine the chemical condition indicated by each pad based on the comparison; and
instructions configured to communicate via the transmitter 108 using a communications protocol 118 the determined chemical condition to a user or a treatment device via the transmitter.

In one form, the mobile device 104 communicates with a treatment system 130 for treating a fluid such as water. A receiver 132 is configured to communicate with the transmitter 108 and configured to receive a signal 134 from the transmitter 108 indicative of the determined chemical condition of the fluid. A treatment device 136 treats the fluid; for example, the treatment device 136 comprises a mixing device such as a mixing valve for adding one or more fluids/chemicals to the fluid for altering the chemical condition of the fluid. Alternatively or in addition, the treatment device 136 comprises a fluid altering device such as an ionization chamber, a heating/cooling device, a sterilizer, and/or a filter. In one embodiment of a system for treating pool/spa, the mixing device comprises a device for adding chlorine for low chlorine levels or adding a chlorine neutralizing chemical such as sodium thiosulfate or hydrogen peroxide for high chlorine levels. A controller 138 is connected to the treatment device 136 and connected to and responsive to the receiver 132. The treatment device 136 is responsive to the controller 138. The controller 138 is configured to determine a treatment to the fluid as a function of the received signal 134 received by the receiver 132, which signal 134 is indicative of the condition of the fluid being treated. The controller 138 controls the treatment device 136 to treat the fluid in accordance with the determined treatment.

As a specific example, consider a granular chlorine feeder system for treating pool/spa water. A user tests the water with one or more test strips 102 to determine such water parameters as free chlorine, pH, and cyanuric acid of the water. The camera 112 of the mobile device evaluates the test strip(s) 102 and the APP 116 determines the chlorine level in the water based on the measured free chlorine, pH, and cyanuric acid as indicated by the test strip(s). Alternatively or in addition, the water temperature can also be determined by the user and manually input to the APP 116 as a parameter to assist in determining the chlorine level. The determined chlorine level is transmitted by the mobile device to the granular chlorine feeder system which adds chlorine to the water in the event that the determined chlorine level is below a preset minimum. This provides an accurate system and method for managing chlorine in the water because the minimum safe chlorine level depends upon the pH, cyanuric acid, and/or temperature of the water.

In an embodiment, aspects of the invention associate colors present in a captured image with colors indicative of a chemical condition (e.g., chlorine level) of a solution to alter aspects of a treatment device for altering the chemical condition. In a further embodiment, a chemical condition of a fluid indicated by test strip 102 causes the APP 116 to display the chemical condition via a graphical user interface of the display of mobile device 104. In yet another embodiment, a chemical condition of a fluid indicated by test strip 102 causes the APP 116 to communicate with the treatment system 130 via a communication network when the chemical condition indicates that an action needs to be implemented by the treatment system 130.

The Abstract and summary are provided to help the reader quickly ascertain the nature of the technical disclosure. They are submitted with the understanding that they will not be used to interpret or limit the scope or meaning of the claims. The summary is provided to introduce a selection of concepts in simplified form that are further described in the Detailed Description. The summary is not intended to identify key features or essential features of the claimed subject matter, nor is it intended to be used as an aid in determining the claimed subject matter.

For purposes of illustration, programs and other executable program components, such as the operating system, are illustrated herein as discrete blocks. It is recognized, however, that such programs and components reside at various times in different storage components of a computing device, and are executed by a data processor(s) of the device.

Although described in connection with an exemplary computing system environment, embodiments of the aspects of the invention are operational with numerous other general purpose or special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well-known computing systems, environments, and/or configurations that may be suitable for use with aspects of the invention include, but are not limited to, personal computers, server computers, handheld or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the aspects of the invention may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the invention may also be practiced in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the invention.

Embodiments of the aspects of the invention may be implemented with processor-executable instructions. The processor-executable instructions may be organized into one or more processor-executable components or modules on a tangible processor readable storage medium which is not a signal. Aspects of the invention may be implemented with any number and organization of such components or modules. For example, aspects of the invention are not limited to the specific processor-executable instructions or the specific components or modules illustrated in the figures and described herein. Other embodiments of the aspects of the invention may include different processor-executable instructions or components having more or less functionality than illustrated and described herein.

The order of execution or performance of the operations in embodiments of the aspects of the invention illustrated and described herein is not essential, unless otherwise specified. That is, the operations may be performed in any order, unless otherwise specified, and embodiments of the aspects of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the aspects of the invention are achieved and other advantageous results may be attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the aspects of the invention by way of example and not by way of limitation. This description enables one skilled in the art to make and use the aspects of the invention, and describes several embodiments, adaptations, variations, alternatives and uses of the aspects of the invention, including what is presently believed to be the best mode of carrying out the aspects of the invention. Additionally, it is to be understood that the aspects of the invention is not limited in its application to the details of construction and the arrangement of components set forth in the following description or illustrated in the drawings. The aspects of the invention are capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. It is contemplated that various changes could be made in the above constructions, products, and methods without departing from the scope of aspects of the invention. In the preceding specification, various preferred embodiments have been described with reference to the accompanying drawings. It will, however, be evident that various modifications and changes may be made thereto, and additional embodiments may be implemented, without departing from the broader scope of the aspects of the invention as set forth in the claims that follow. The specification and drawings are accordingly to be regarded in an illustrative rather than restrictive sense.

What is claimed is:

1. A computer readable storage device having processor executable instructions stored thereon comprising an APP, said APP including instructions that, when executed by a processor of a mobile device, implement a method of indicating a chemical condition, comprising:
   reading a test strip via a camera of the mobile device;
   locating a first code at a first location on the test strip;
   locating a second code at a second location on the test strip, wherein a distance between the first code and the second code comprises a code interval;
   locating one or more pads each at separate locations on the test strip within a region of interest thereof relative to a position of the located first code on the test strip by utilizing the code interval to determine distances between the one or more pads on the test strip;
   determining a color of each located pad;
   comparing each determined color to a corresponding reference stored in a memory device of the mobile device;
   determining the chemical condition indicated by each pad based on the comparison; and
   communicating the determined chemical condition to a user via a display of the mobile device or a treatment device via a transmitter of the mobile device.

2. The computer readable storage device of claim 1 wherein the test strip comprises a substrate, and wherein the one or more pads on the test strip each comprise a color-sensitive pad on the substrate for sensing the chemical condition and providing a color in response to the sensed chemical condition.

3. The computer readable storage device of claim 1 wherein the first and second codes each comprise at least one of a bar code and a QR code.

4. The computer readable storage device of claim 1, said APP further comprising instructions that, when executed by the processor of the mobile device, color calibrate the camera based on a hue of the located code.

5. The computer readable storage device of claim 4, wherein the camera is color calibrated specifically for said locating the one or more pads on the test strip.

6. The computer readable storage device of claim 1, wherein the first code and the second code each serve as a point defining a line along which the one or more pads are located on the test strip.

7. A system for use with a test strip configured to indicate a chemical condition comprising:
   a mobile device having a processor, a transmitter, a memory device, and a camera configured to read the test strip, an APP comprising processor executable instructions configured to be stored in the memory device and configured to be executed by the processor, said instructions comprising:
   instructions configured to detect a first code at a first location on the test strip;
   instructions configured to detect a second code at a second location on the test strip, wherein a distance between the first code and the second code on the test strip comprises a code interval;
   instructions configured to detect one or more pads each at separate locations on the test strip by utilizing the code interval and a region of interest relative to the location of the detected first code within which the one or more pads are located;
   instructions configured to determine a color of each detected pad;
   instructions configured to compare each determined color to a corresponding reference stored in the memory device;
   instructions configured to determine the chemical condition indicated by each pad based on the comparison; and
   instructions configured to communicate the determined chemical condition to a user or a treatment device via the transmitter.

8. The system of claim 7 further comprising instructions for color calibrating the camera based on a color of the located code.

9. The system of claim 8, wherein the instructions for color calibrating the camera calibrate the camera specifically for the instructions configured to locate the one or more pads on the test strip.

10. The system of claim 7 wherein the test strip comprises:
    a substrate;
    wherein the one or more pads each comprise a color-sensitive pad on the substrate for sensing a chemical condition and providing a color in response to the sensed chemical condition; and
    wherein the first and second codes each comprise a code on the substrate.

11. The system of claim 7 wherein the first and second codes each comprise at least one of a bar code and a QR code.

12. The system of claim 7, wherein the locations of the first code and the second code each serve as a point defining a line along which the one or more pads are located on the test strip.

13. A system comprising:
    a test strip configured to indicate a chemical condition, the test strip including a first code at a first location thereon, a second code at a second location thereon, and one or more pads each at separate locations thereon;
    a mobile device having a processor, a transmitter, a memory device, and a camera configured to acquire an image of the test strip, an APP comprising processor executable instructions configured to be stored in the memory device and configured to be executed by the processor, said instructions comprising:
    instructions configured to locate the first and second codes in the acquired image of the test strip;
    instructions configured to locate the one or more pads within a region of interest of the acquired image of the test strip relative to the located first code by utilizing a distance between the location of the first code and the location of the second code;
    instructions configured to determine a color of each located pad;
    instructions configured to compare each determined color to a corresponding reference stored in the memory device;
    instructions configured to determine the chemical condition indicated by each pad based on the comparison; and instructions configured to communicate the determined chemical condition to a user or a treatment device via the transmitter.

14. The system of claim 13 wherein the test strip comprises:
a substrate;
wherein the pads comprise a plurality of color-sensitive pads on the substrate for sensing a chemical condition and providing a color in response to the sensed chemical condition; and
wherein the first and second codes each comprise a code on the substrate.

15. The system of claim 13 wherein the first and second codes each comprise at least one of a bar code and a QR code.

16. The system of claim 13, further comprising instructions for color calibrating the camera specifically for locating the one or more pads on the test strip based on a hue of the located code.

17. The system of claim 13, wherein the first code and the second code each serve as a point defining a line along which the one or more pads are located on the test strip.

18. The system of claim 13, wherein the distance between the location of the first code and the location of the second code comprises a code interval.

* * * * *